(12) United States Patent
Grossman et al.

(10) Patent No.: US 6,679,095 B1
(45) Date of Patent: Jan. 20, 2004

(54) MULTI-TEST GRAVELOMETER

(75) Inventors: Douglas M. Grossman, Fairview Park, OH (US); Steven J. Grossman, Lakewood, OH (US); Gary J. Billington, Fairview Park, OH (US)

(73) Assignee: Q-Panel Lab Products Corporation, Westlake, OH (US)

( * ) Notice: Subject to any disclaimer, the term of this patent is extended or adjusted under 35 U.S.C. 154(b) by 0 days.

(21) Appl. No.: 09/600,280

(22) PCT Filed: Jan. 26, 1999

(86) PCT No.: PCT/US99/02037

§ 371 (c)(1),
(2), (4) Date: Jul. 13, 2000

(87) PCT Pub. No.: WO99/39179

PCT Pub. Date: Aug. 5, 1999

Related U.S. Application Data

(60) Provisional application No. 60/072,840, filed on Jan. 28, 1998.

(51) Int. Cl.[7] .............................. G01N 3/56; G01N 3/62
(52) U.S. Cl. ........................... 73/7; 73/12.01; 73/150 R
(58) Field of Search ..................... 73/7, 150 R, 150 A, 73/11.02, 12.01; 72/53; 29/428, 890.09, 464, 466, 559, DIG. 36; 451/38, 64

(56) References Cited

U.S. PATENT DOCUMENTS

| | | | |
|---|---|---|---|
| 3,509,086 A | 4/1970 | Rohrbacher, Jr. | |
| 4,239,808 A | 12/1980 | Arnason | 428/482 |
| 5,250,807 A | * 10/1993 | Sontvedt | 250/303 |
| 5,750,878 A | 5/1998 | Bliss | 73/1.79 |
| 5,938,509 A | * 8/1999 | Fox et al. | 324/701 X |

FOREIGN PATENT DOCUMENTS

| | | | |
|---|---|---|---|
| DE | 34 16 973 C2 | 11/1984 | G01N/3/32 |
| DE | 37 40 817 A1 | 6/1989 | 451/88 |
| EP | 0 434 663 A1 | 6/1991 | G01N/3/50 |

OTHER PUBLICATIONS

Research Publication GMR–767, Donal R. Hass The Measurement of Chipping of Automotive Finishes May 1968, cover page, pp. 1–14 & 8 page Appendix.*
Designation: D3170–74 (Reapproved 1980) American Society for Testing Material "Standard Test Method for Chip Resistance of Coatings" Sep. 1980 pp. 645–648.*
Q–G–R Gravelometer Adhesion Tester 2 page Product brochure published by Jan. 1998 (L–890).*
Q–Panel, Q–G–R Gravelometer Operating Instructions, 2 page Product Brochure Published by Jan. 1998 (L–895).*
Erichsen, "Technical Description and Operating Instructions, 508/E VDA Stone Hammer Blow Testing Instrument, Model 508", Jun. 1992, 5 pages.*
Q–Panel Lab Products, Multi–Test Grave Gmeter Impact Tester Operating Manual, Jan. 15, 1998, pp 1–41.*

* cited by examiner

*Primary Examiner*—Thomas P. Noland
(74) *Attorney, Agent, or Firm*—Fay, Sharpe, Fagan, Minnich & McKee, LLP (57) ABSTRACT

A gravelometer (20) includes a base unit (30) comprising compressed air receiver tank (40) having wheels (42) and feet (44). Main frame (46) connects tank (40) to a media gun frame or mount (50) and includes a bore (52) for releasably receiving and supporting a media gun (54) having a mounting flange (70) so that media inlet (56) is upwardly oriented and gun barrel or media outlet (57) extends through gun mount (50). Media inlet (56) interconnects via elongated con-duit (58) to a media supply system (60) which includes media supply hopper (62) and vibratory feeder assembly (64). A control system (80) having operator control panel (82) controls operations. A modular target box or chamber (90) is aided in being releasably connected to base unit (30) by locator pins (102). Chamber (90) includes media inlet (92), media outlet (94), which connects to spent media reclaim chamber (100), and specimen window (96) having a target holding toggle clamp (98).

10 Claims, 11 Drawing Sheets

FIG.13B

MULTI-TEST GRAVELOMETER

This application claims priority from and benefit of the filing date of U.S. provisional application Ser. No. 60/072,840 filed Jan. 28, 1998.

BACKGROUND OF THE INVENTION

The present invention relates generally to an apparatus for testing the chipping resistance and adherence of surface coatings. More particularly, the invention relates to a gravelometer having multi-standard capabilities so that a user need not purchase a plurality gravelometers each dedicated to a particular testing standard. In accordance with the present invention, a gravelometer base unit selectively receives one of a plurality of target chambers to enclose the sample being tested, and one of a plurality of media guns for propelling the media at the test sample secured in the target chamber. The particular target chamber and media gun utilized depend upon the particular testing standard to be followed.

Gravelometers and their use for testing the adhesion and chip resistance of coatings to a test panel or other specimen are generally well known. Typically, the gravelometer is adapted to project a specified volume of standardized blasting media, such as gravel, split shot, buck shot, sand, or the like, at a test panel or other object coated with the paint or other coating being tested. The test panel is housed in or otherwise surrounded by a "target chamber" so that the media is contained for safety. The media is typically propelled toward the test specimen from a media "gun" under the Force of compressed air at a specified pressure and flow rate. Media is fed into the media gun in a controlled manner either manually or through use of an automatic feeding apparatus. Once the supply of media is exhausted, the test panel is removed from the target chamber, examined, and evaluated in accordance with particular chipping and adherence standards.

In the United States of America, gravelometers, their use, and test specimen evaluation, are generally carried out in accordance with Recommended Practice SAE J400 of the Society of Automotive Engineers (SAE J400). In general, SAE J400 specifies test equipment, test conditions, test procedures, and test specimen evaluation. More particularly, SAE J400 specifies the use of a particular media (standardized gravel), a particular compressed air gun for projecting the gravel, a particular distance between the test specimen and the gun, particular angular orientations of the test specimen relative to the projection path of the media, and other testing parameters. As such, heretofore, those desiring to test coatings in accordance with SAE J400 were required to purchase a dedicated SAE J400 compliant gravelometer not usable to conduct testing in accordance with any other standard.

Likewise, those desirous of testing a specimen in accordance with a common European standard established by Verband der Automobilindustrie (VDA), had to purchase a dedicated VDA compliant gravelometer. The SAE J400 and VDA standards use different media and different types of media guns. Therefore, neither a dedicated SAE J400 gravelometer nor a dedicated VDA gravelometer is usable to conduct coating tests under a different standard.

In addition to being generally inconvenient, the need to purchase, operate, and maintain multiple prior gravelometers was found to be quite expensive and generally undesirable. Also, the multiple gravelometers consume large amounts of valuable shop floor space.

Another problem associated with prior gravelometers is their inability to receive and contain large three-dimensional test specimens. For example, with coatings, it is often desirable to test the chipping resistance after the coating has been applied to an actual end product such as a wheel, a spring, or an automobile body part. With prior gravelometers, their is no convenient and effective way of subjecting such three-dimensional objects to a test without departing from the test procedures or without purchasing yet another specialized gravelometer made for such parts.

SUMMARY OF THE INVENTION

The present invention therefore relates to a gravelometer which is able to belconfigured with any one of a plurality of target chambers and media guns to comply with SAE J400, VDA, or any other testing standard.

In accordance with a first aspect of the invention, a gravelometer apparatus includes a media gun mount extending from a frame member. The gun mount includes a bore adapted to receive a barrel of an associated media gun and a media gun fastening device for fixedly and releasably securing the media gun relative to the mount so that the gun barrel is placed in the bore. A first enclosed target chamber is releasably secured to the frame member in an operative position so that the barrel of an associated media gun secured to the frame member is directed into an enclosed interior space of the target chamber through an inlet. The target chamber includes a target support for fixedly retaining a target specimen in an operative position so that testing media projected outwardly from an outlet in the barrel of the associated gun impinges upon the target specimen and is retained in the enclosed interior space. A media supply system is connected to the frame member and included a media hopper and a media feeder for conveying media from the hopper to a media inlet of the associated media gun.

In accordance with another aspect of the present invention, a multi-test gravelometer for performing coating testing operations based on at least two different standards includes a frame adapted for releasably receiving and retaining an associated one of at least first and second media guns in an operative position so that a media inlet of the gun is positioned to receive testing media and a media outlet of the gun is positioned to project testing media toward a testing target. A compressed air supply is adapted for communication with an air inlet of the gun. The gravelometer includes means for selectively and releasably connecting one of a plurality of different two-dimensional specimen target chambers to the frame by in an operative position so that the media outlet of the gun is directed into and enclosed by an interior portion of the target chamber in line with a target specimen support region thereof.

In accordance with still another aspect of the present invention, a modular gravelometer apparatus includes a base unit having a frame. A compressed air tank is secured to the frame. A plurality of different media guns, each conformed in accordance with a particular testing standard, are adapted for individual and selective operative securement to the base unit frame by at least one releasable connector. Each of the media guns includes a media inlet adapted to receive testing media, a media outlet for projecting the testing media outwardly along a target path, and a compressed air inlet adapted for selective fluid communication with the compressed air tank. A plurality of different two-dimensional specimen target chambers are each conformed in accordance with one of the testing standards and adapted for individual and selective securement to the base unit in an operative position using at least one releasable connector. Each target chamber defines an enclosure, a media inlet to the enclosure, and an air exhaust vent, and each chamber includes a target specimen securement device for selectively and releasably securing a target specimen in an operative position in line with the target path so that testing media projected from an operatively secured media gun impinges on the operatively secured target specimen.

In accordance with yet another aspect of the present invention, a method of constructing a gravelometer apparatus to perform testing in accordance with one of at least two different testing standards includes selecting one of a plurality of different media projecting guns. Each of the guns is conformed in accordance with a different testing standard. The selected gun is operatively and releasably secured to a frame member. One of a plurality of different target chambers is selected to correspond with the selected one: of the media guns. Each chamber is conformed in accordance with one of the different testing standards. The selected chamber is operatively and releasably securing to the frame member so that a testing media outlet of the operatively secured media gun is directed into an enclosed interior portion of the operatively secured target chamber. An air inlet of the operatively secured media gun is connected to a supply of compressed air.

One advantage of the present invention is that it eliminates the need for multiple gravelometers each dedicated to a particular testing standard.

Another advantage of the present invention is that it provides a gravelometer base unit to which any one of a plurality of media guns and many one of a plurality of target chambers are easily and conveniently connected to construct a gravelometer in accordance with any testing standard.

Still another advantage of the present invention is that a three-dimensional specimen target chamber is easily and selectively connectable to any of the target chambers as needed for testing three-dimensional specimens in accordance with any testing standard.

Yet another advantage of the present invention is that a wide variety of blast media such as gravel, split shot, buckshot, sand, or MDOT 25A, is able to be used for testing procedures.

A further advantage of the present invention is that it is more easily and less expensively repaired or calibrated.

Still other benefits and advantages of the invention will become readily apparent to those skilled in the art upon reading and understanding the following detailed specification.

BRIEF DESCRIPTION OF THE DRAWINGS

The invention may take physical form in certain parts and arrangements of parts, and be carried out in certain steps and arrangements of steps, preferred embodiments of which will be described in detail in this specification and illustrated in the accompanying drawings which form a part hereof and wherein.

DETAILED DESCRIPTION OF THE PREFERRED EMBODIMENTS

With reference now to!FIGURES 1–4, a gravelometer in accordance with the present invention is illustrated generally at 20. The gravelometer includes a base unit 30 to which modular components are selectively connected as is described in detail below. The base unit 30 comprises a source of compressed air (or other gas) which may be a receiver tank 40 connected to al shop air supply or another source. The tank 40 is supported above a shop floor by a combination of wheels 42 and feet 44 that facilitate movement of the gravelometer 20 as desired.

The base unit 30 also includes a main frame 46 connected to the upper region of the tank 40. A media gun frame or mount 50 is connected to the main frame (or formed as a one-piece construction therewith) and includes a bore 52 or other means for releasably receiving a media gun 54 and operatively supporting the gun so that a media inlet 56 of the gun is upwardly oriented and so that the gun barrel (media outlet) 57 extends through the gun mount 50.

As shown herein, the media inlet 56 of the gun 54 is connected to an elongated conduit 58. An open upper end of the conduit 58 is in communication with an automatic media supply system 60. The media supply system 60 receives and retains a supply of gravel or other blast media in a hopper 62 and includes means for dispensing the media from the hopper into the, gun inlet conduit 58 in a controlled manner. As shown herein, the dispensing means comprises a vibratory feeder assembly 64 supported by the frame 50, although any other suitable feeding means may be employed. Alternatively, an operator of the apparatus 20 is able to manually control the flow of media into the gun inlet 56.

Figure 1:
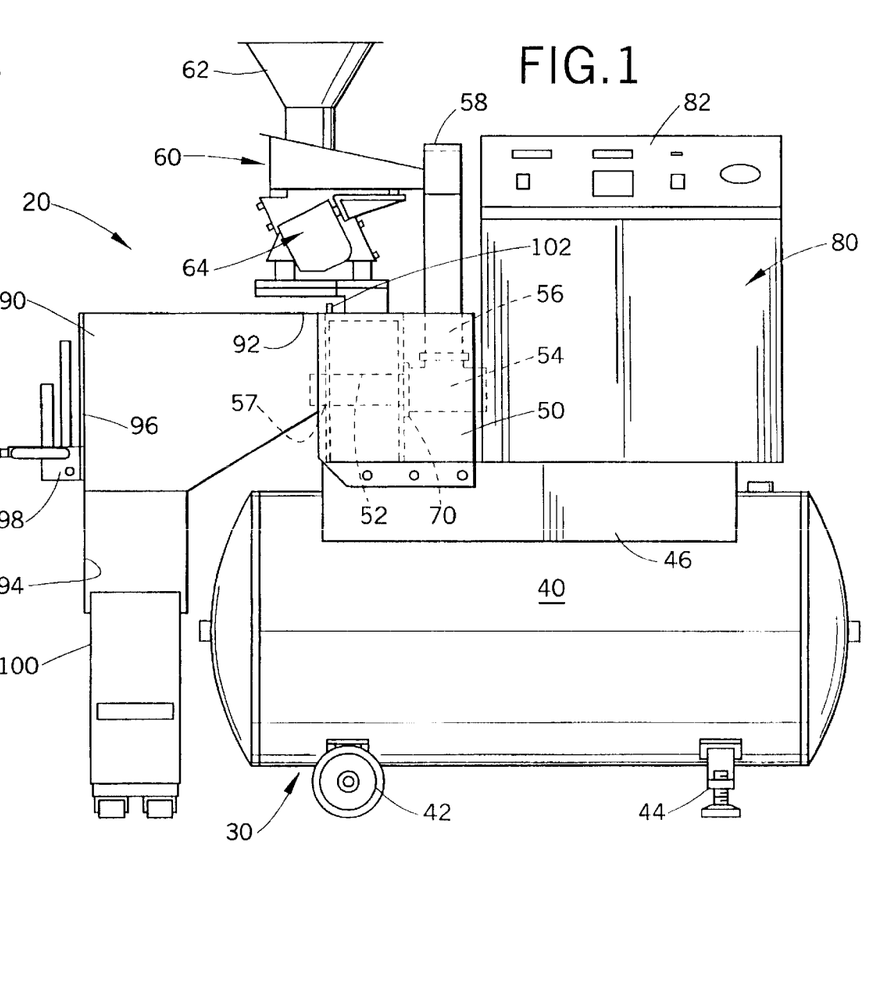
FIG. 1 is a front elevational view of a gravelometer in accordance with the present invention.
Figures 2, 3:
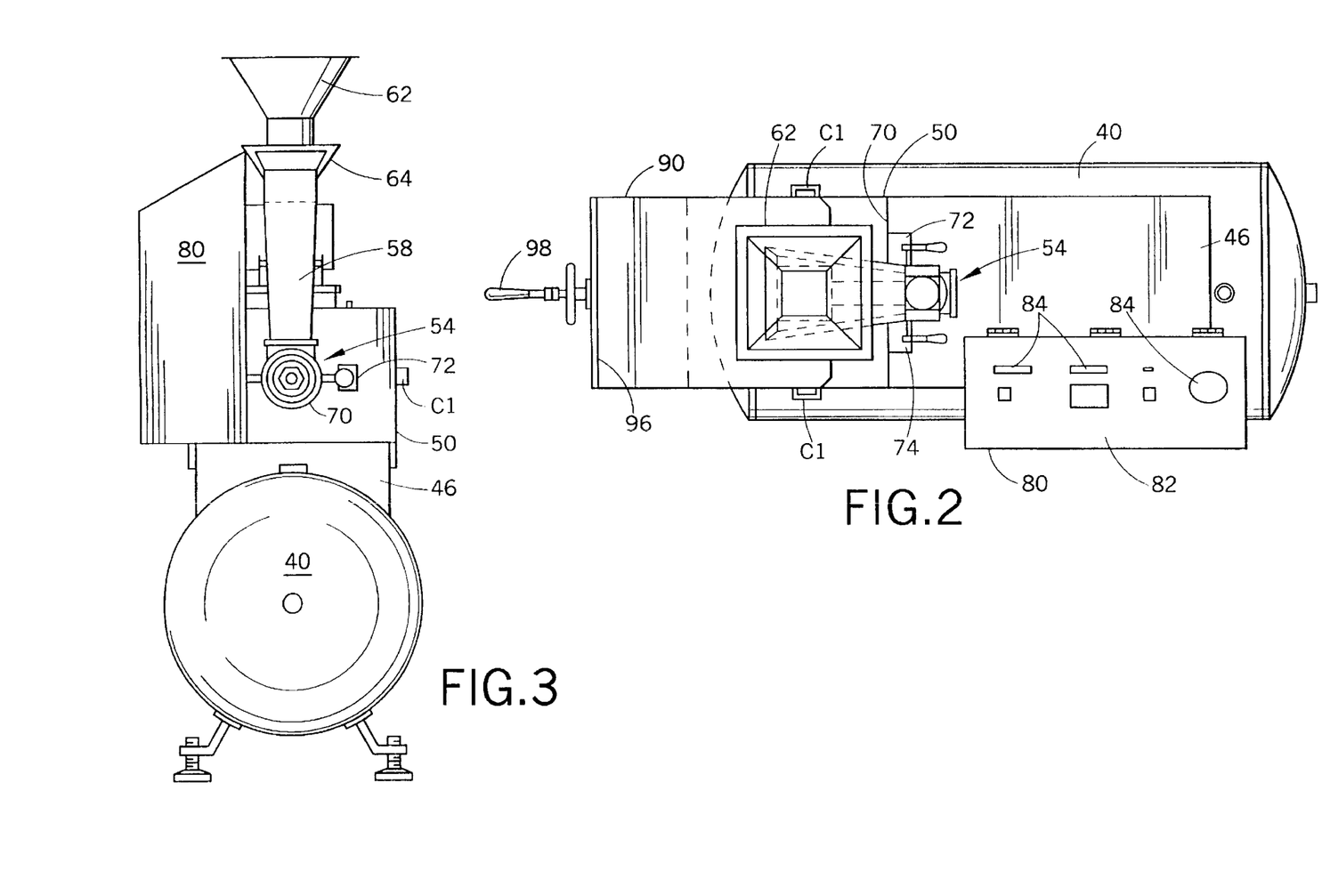
FIG. 2 is a top plan view of the gravelometer shown in FIG. 1.
FIGS. 3 and 4 are right and left side elevational views of the gravelometer shown in FIG. 1, respectively.
Figure 4:
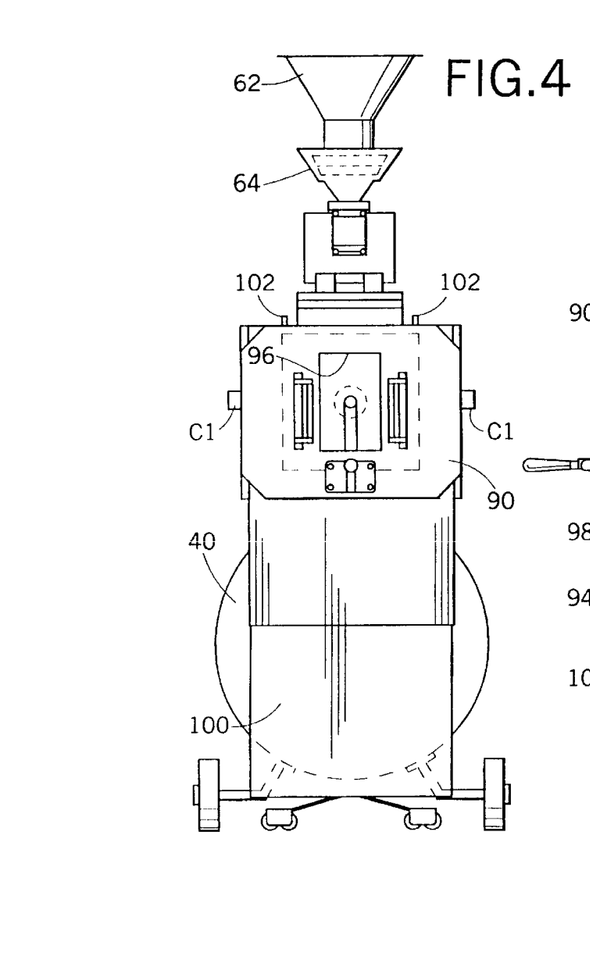

FIGS. 2–4 illustrate the preferred means for selectively, operatively, and releasably securing a modular media gun 54 to the gun frame 50 in accordance with the present invention. A modular SAE J400 compliant media gun 54 in accordance with the present invention includes a radially enlarged mounting flange 70 (see also FIGS. 5–7) that lies adjacent to a face of the frame 50 when the gun is operatively supported by the frame as described. The apparatus 20 includes means for releasably engaging the gun 54 and securing the gun in the operative position without requiring use of wrenches, screwdrivers, or like tools—i.e., through use of manually operable connectors. For example, as shown herein, first and second toggle clamps 72,74 (FIG. 2) are provided to selectively and releasably engage the radially enlarged mounting flange 70 of the gun and prevent any movement of the gun 54 relative to the gun frame 50. Alternatively, the gun may be operatively secured to the frame 50 via means such as a collar assembly, a threaded or key-like connection, bolts, pins, or other fasteners, or any other suitable means that allows the gun 54 to be quickly and easily affixed to and separated from the frame 50. Mating locator pins/apertures or the like are preferably provided on the gun/frame to ensure proper installation and alignment of the gun 54.

Figure 5:
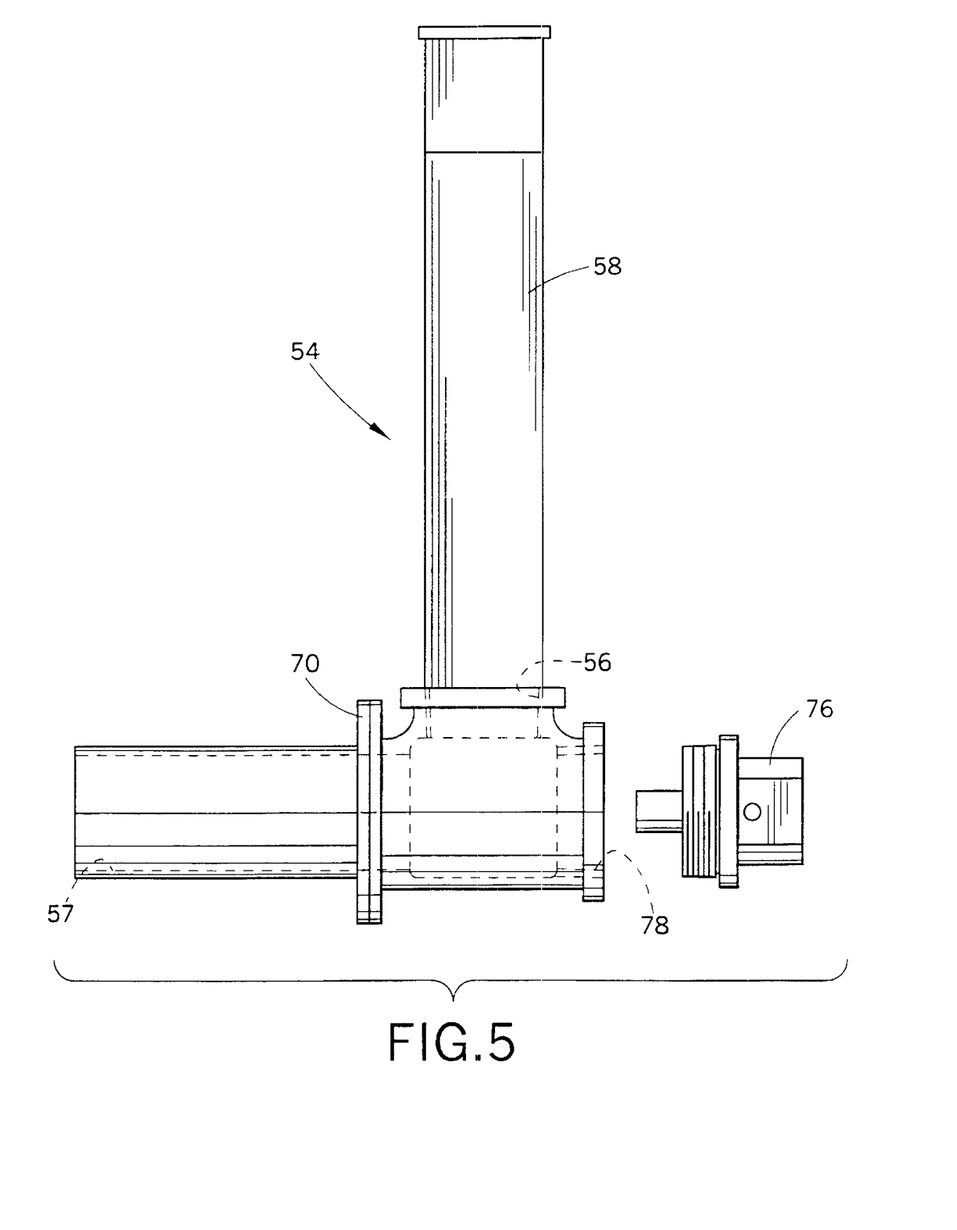
FIG. 5 is an exploded front elevational view of a modular SAE J400 media gun in accordance with the present invention.
Figure 6:
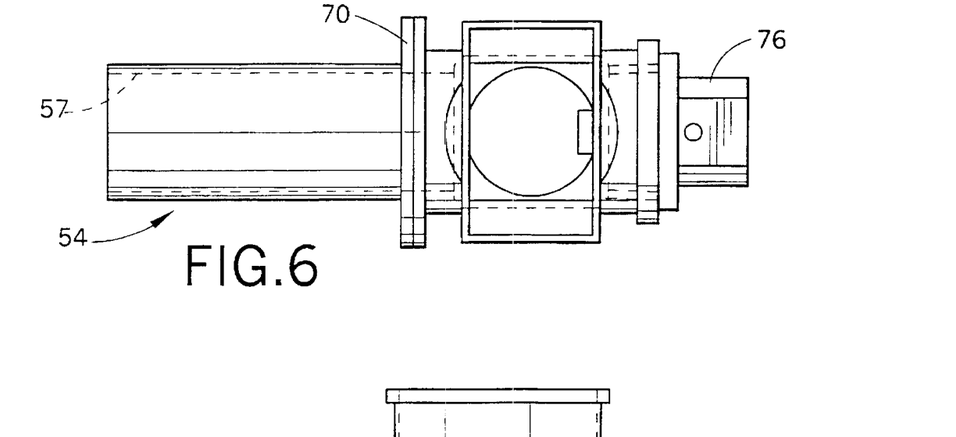
FIG. 6 is a top plan view of the SAE J400 gun shown in FIG. 5, with the gun fully assembled.
Figure 7:
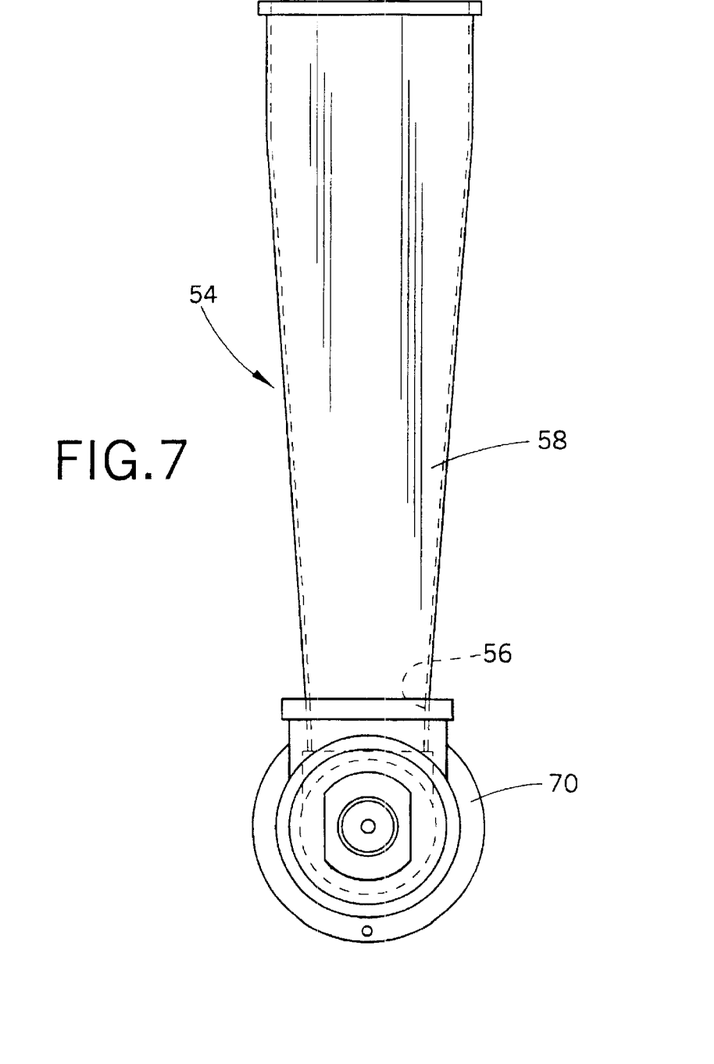
FIG. 7 is a right side elevational view of the SAE J400 media gun shown in FIG. 6.

As is shown in FIGS. 5 and 6, the modular SAE J400 gun comprises an air nozzle 76 which threadably or otherwise mates in a fluid-tight manner with a compressed air inlet 78. The nozzle 76 is connected to the compressed air supply 40 using suitable conduit and one or more valves that allow the selective flow of compressed air to the gun nozzle 76.

Figure 8:
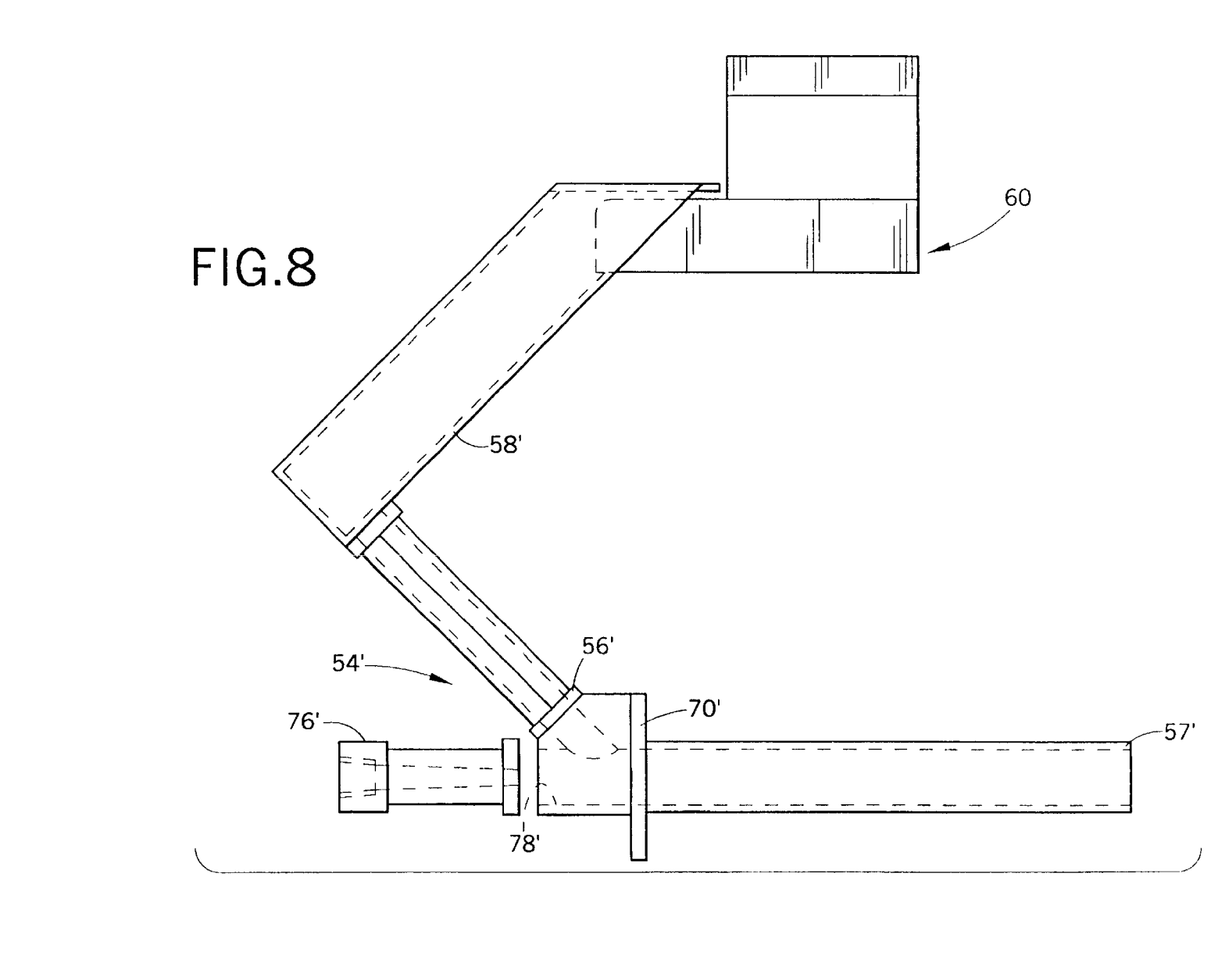
FIG. 8 is a front elevational view diagrammatically illustrating a modular VDA media gun and its connection with a media supply system in accordance with the present invention.

FIG. 8 diagrammatically illustrates an alternative media gun 54' that complies with VDA testing standards rather than SAE standards. Like components relative to the SAE J400 gun 54 are indicated using like reference numerals with a primed (') suffix. Other than having a slightly different configuration and different dimensions, the guns 54,54' are similar in all respects. Also, the gun 54' is preferably used to propel chill-cast iron abrasive. Thus, those skilled in the art will recognize that either gun 54,54', or a gun manufactured in accordance with another standard and the present invention, is selectively, operatively, and releasably connectable to the gun support frame 50 of the gravelometer base unit 30 as described above and required by a particular testing standard in an easy and convenient manner without use of tools.

With reference again to FIGS. 1 and 2, a control system 80 is connected to the main frame 46 and controls all machine operations. The control system includes an operator control panel 82 having a plurality of operator input/output devices 84 thereon. The control system 80 controls the operation of the media supply system 60 and the flow of compressed air (or other gas) from the supply tank 40 to the nozzle 76,76' of a media gun 54,54' through any suitable conventional hose(s).

In FIGS. 1–4 it is shown that a modular target box or chamber 90 is also selectively, operatively, and releasably connected to the base unit 30 of the gravelometer apparatus 20 by any suitable means such as clips C1, interlocking parts, bolts, pins, or any other fasteners. The target chamber 90 defines an enclosure which shields a test specimen and prevents the escape of the blasting media after it impacts a test specimen. The target chamber 90 includes a media inlet 92, a media outlet 94, and a specimen window 96. When the target chamber is operatively and releasably connected to the base unit 30 as shown, the media inlet 92 seals against the frame 50 to prevent the escape of media and to allow the projection of the media from a gun barrel 57,57' into the chamber 90 along a horizontal projection or target path. The specimen window 96 is aligned with the gun barrel 57,57', and a toggle clamp 98, or other means such as a frame, releasably and firmly secures a flat, two-dimensional test panel or other specimen in the window 96 so that the window is sealed by the specimen and any associated specimen support structure. In this manner, media propelled into the target chamber 90 along the horizontal projection path impinges upon the test sample but is contained within the target chamber. As is described in full detail below, the angular orientation of the test specimen and its distance from the gun barrel 57,57' depends on the particular gun/target chamber combination connected to the base unit 30. As shown herein, the chamber 90 is an SAE J400 compliant target chamber which secures the specimen at a 90° angle relative to the horizontal media projection path. The spent media falls through the media outlet 94 into a media reclaim chamber 100.

Figure 9A:
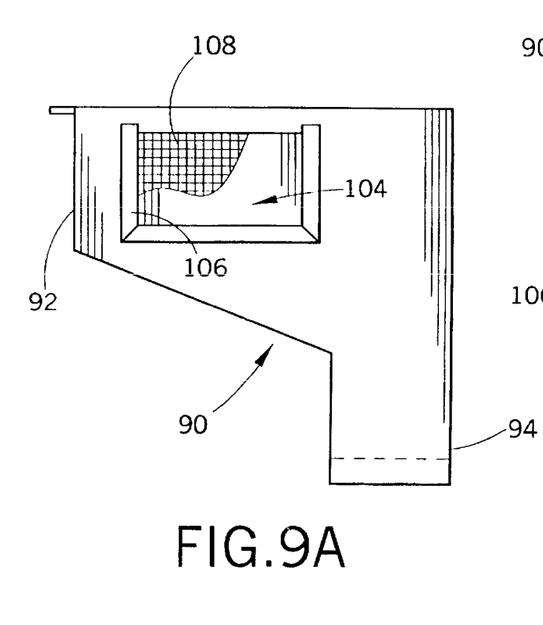
FIGS. 9A–9D are rear elevational, left side elevational, front elevational, and top plan views, respectively, of a modular SAE J400 90° target chamber in accordance with the present invention (with FIGS. 9C and 9D partially broken away)
Figure 9B:
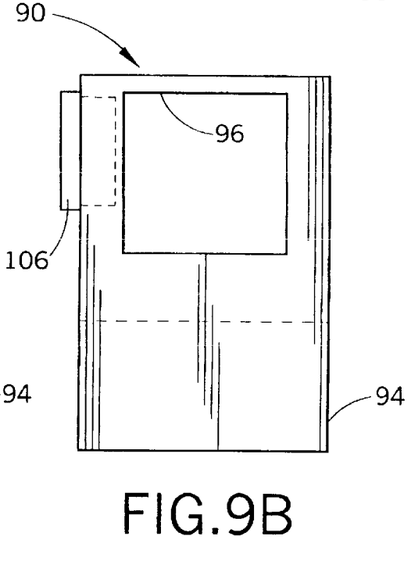
Figure 9C:
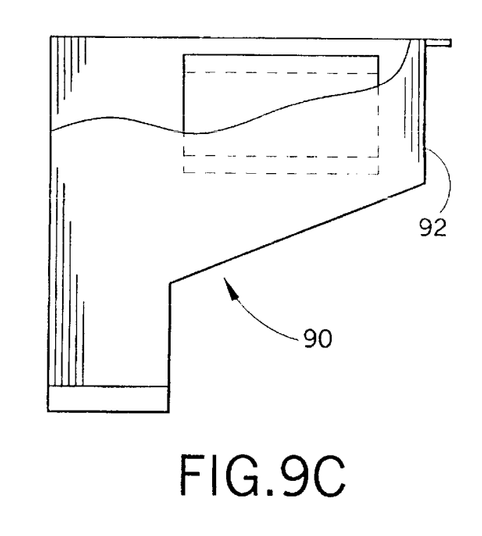
Figure 9D:
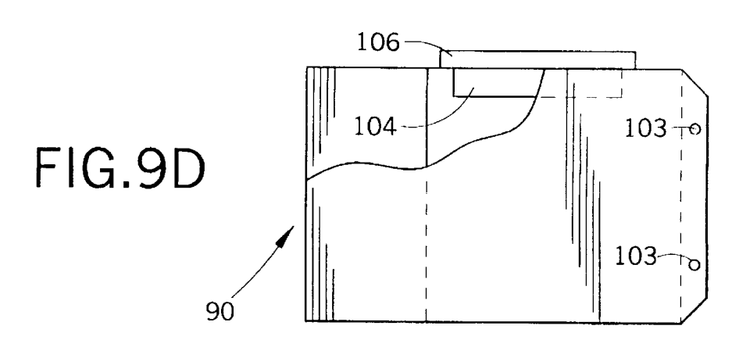
Figures 10A, 10B, 10C, 10D:
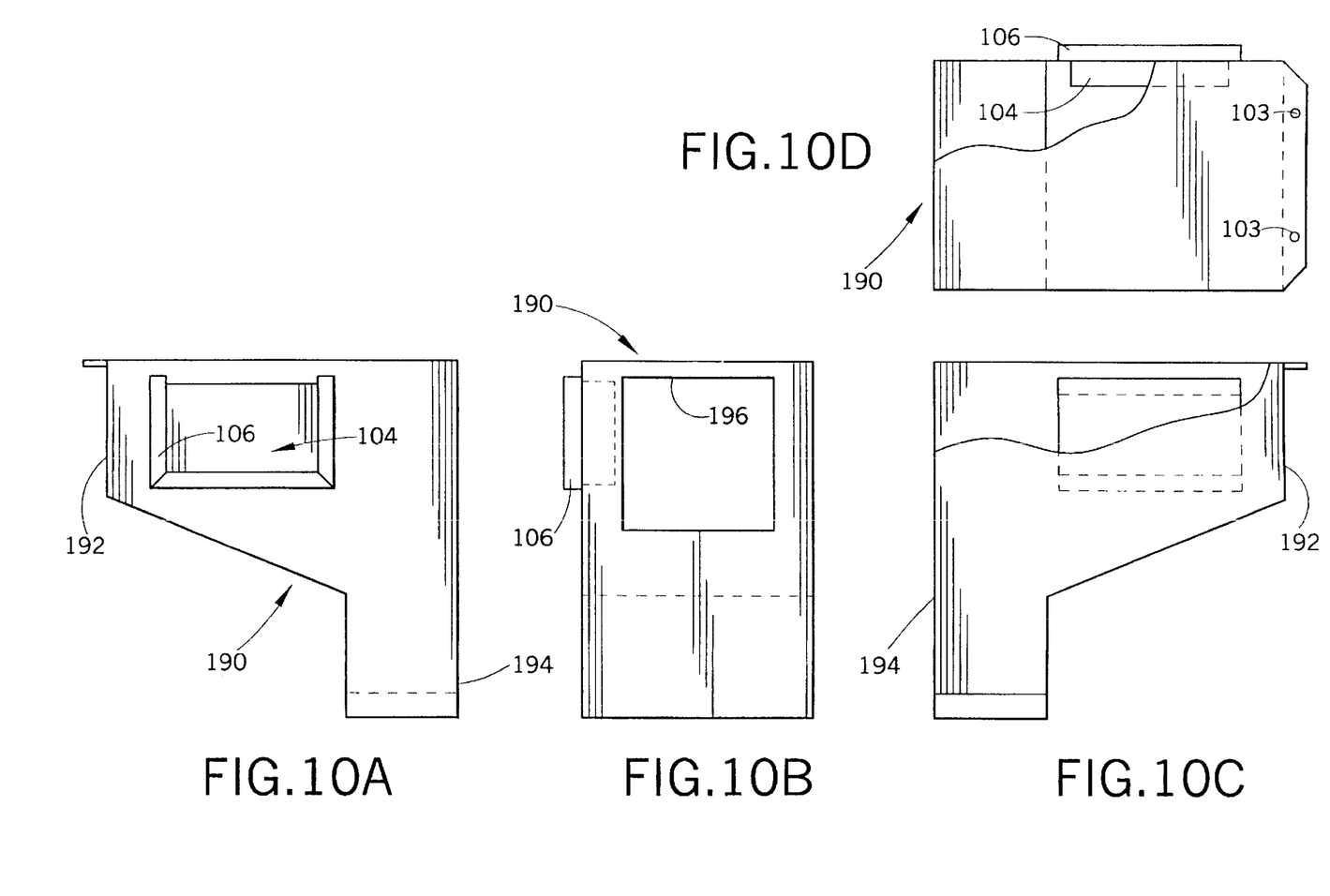
FIGS. 10A–10D are rear elevational, left side elevational, front elevational, and top plan views, respectively, of a modular VDA 90° target chamber in accordance with the present invention (with FIGS. 10C and 10D partially broken away)
Figure 11A:
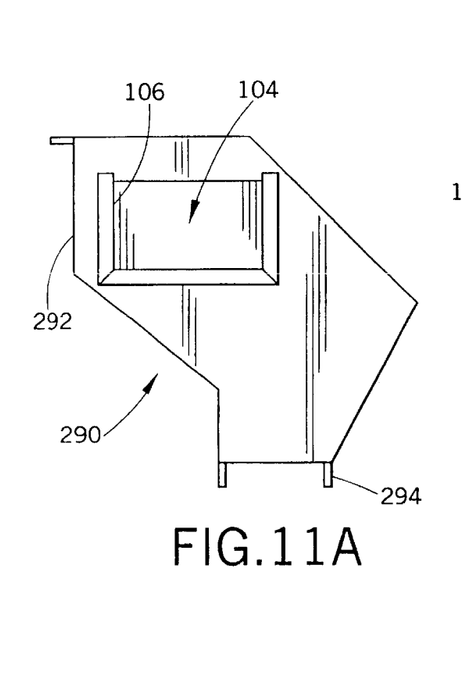
FIGS. 11A–11D are rear elevational, left side elevational, front elevationlal, and top plan views, respectively, of a modular SAE J400 45° target chamber in accordance with the present invention.
Figure 11B:
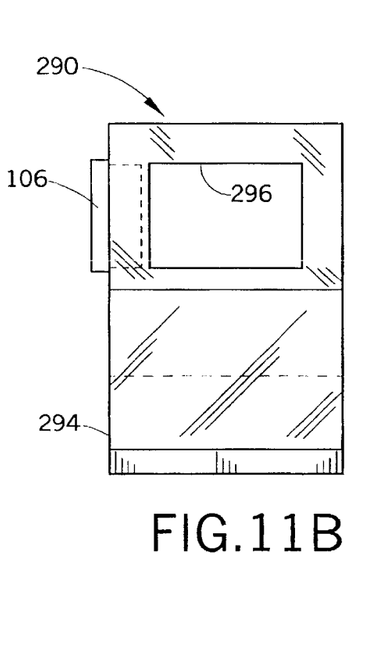
Figure 11C:
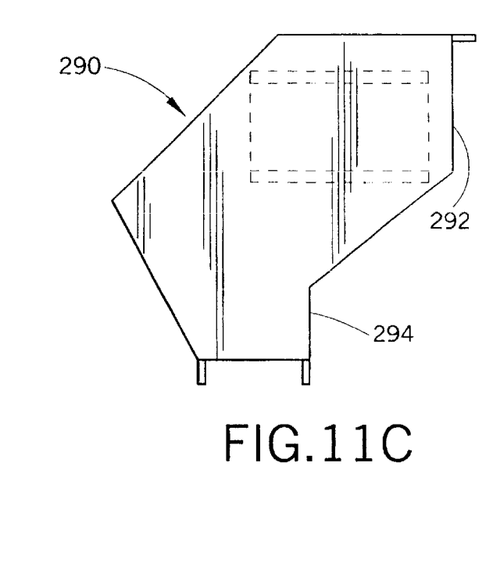
Figure 11D:
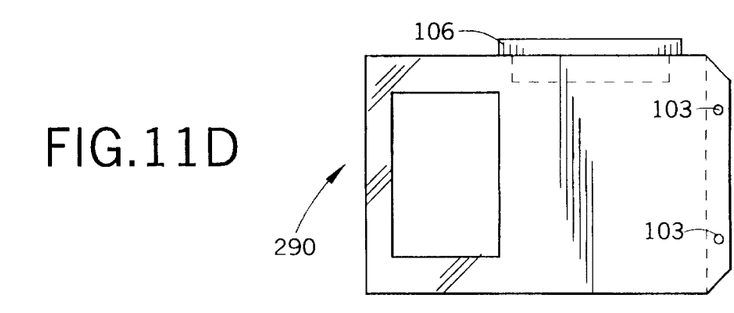
Figures 12A, 12B:
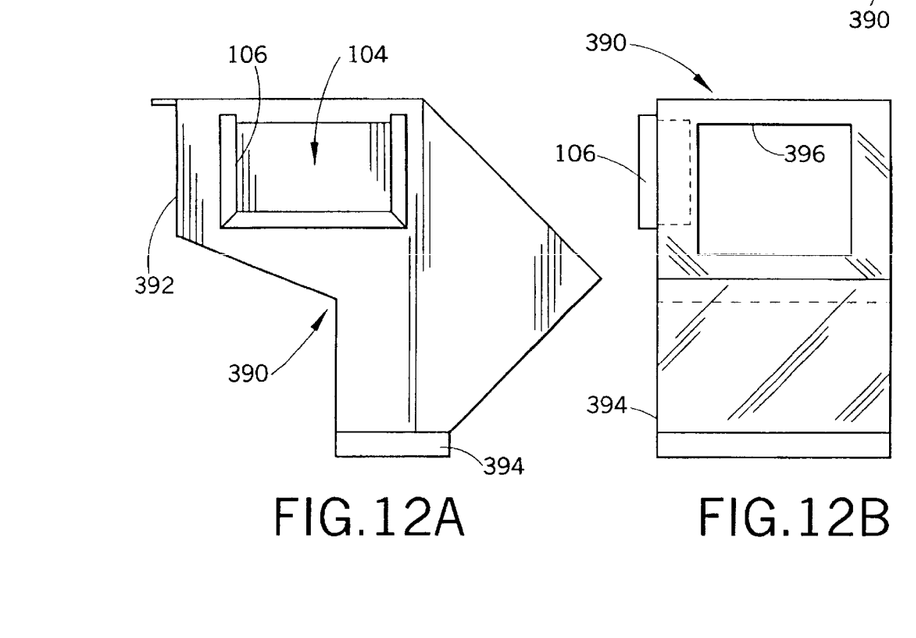
FIGS. 12A–12D are rear elevational, left side elevational, front elevational, and top plan views, respectively, of a modular VDA 45° target chamber in accordance with the present invention.
Figure 12C:
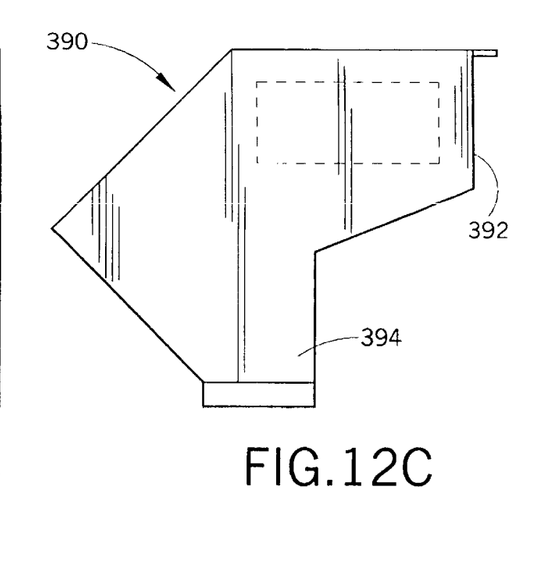
Figure 12D:
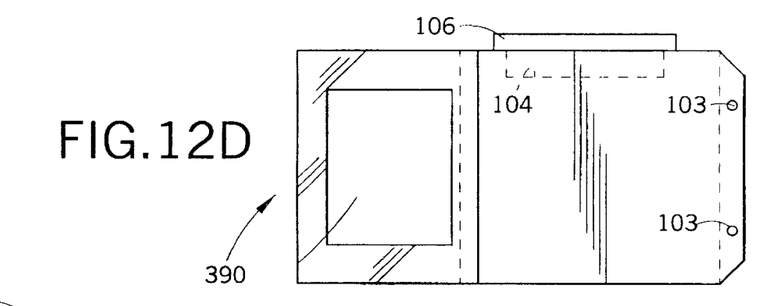

As noted, the subject multi-test gravelometer 20 comprises means for selectively, operatively, and releasably connecting the modular target chamber 90 to the base unit 30 so that any one of a plurality of different modular target chambers may be connected to the base unit as desired to comply with a particular testing standard in an easy and convenient manner without aid of tools. As shown herein, a plurality of clips, clamps, or like connectors C1 (FIGS. 2–4) are utilized. Also, for purposes of facilitating releasable connection of a target chamber 90, it is preferred that the frame 50 include one or more locator pins 102 (FIGS. 1 and 4) that each engage a mating aperture 103 (FIG. 9D) of the target chamber 90 to facilitate the proper interconnection of the chamber 90 and the frame 50. A target chamber safety switch is connected to the control system 80 and senses the proper connection of the target chamber 90 to the frame 50. In the event the chamber 90 is not properly connected to the frame, the control system will not allow operation of the apparatus 20. Of course, the chamber 90 can be releasably connected to the frame 50 through use of any suitable manually operable "quick-disconnect" type retainers.

FIGS. 9A–9D illustrate the SAE J400 90° target chamber 90 in full detail. FIGS. 10A–10D, 11A–11D, and 12A–12D illustrate alternative modular target chambers 190, 290, and 390, respectively, in accordance with the present invention for selective and releasable interconnection to the gravelometer base unit 30 in the same manner as the chamber 90 to comply with al variety of other testing standards as desired. The parts of the modular chambers 190,290,390 relative to the modular chamber 90 are indicated with like reference numerals that are 100, 200, and 300 units greater, respectively, than corresponding parts of the target chamber 90. The modular target chambers 90,190 secure a test specimen at a 90° angle relative to the media projection path while the target chambers 290,390 secure a test specimen at a 45° angle relative to the projection path.

Each modular target chamber 90,190,290,390 also includes a vent opening 104 formed therethrough for the exhaustion of the compressed lair that propels the blast media. A dust filter 108 (FIG. 9A) is secured in the vent opening 104 of each tar get chamber and blocks the passage of airborne particulates through vent opening 104. As shown herein, the filter 108 is secured in the opening 104 through use of a frame 106 which slidably receives the filter. Other filter securement means may be used as desired.

Figure 13A:
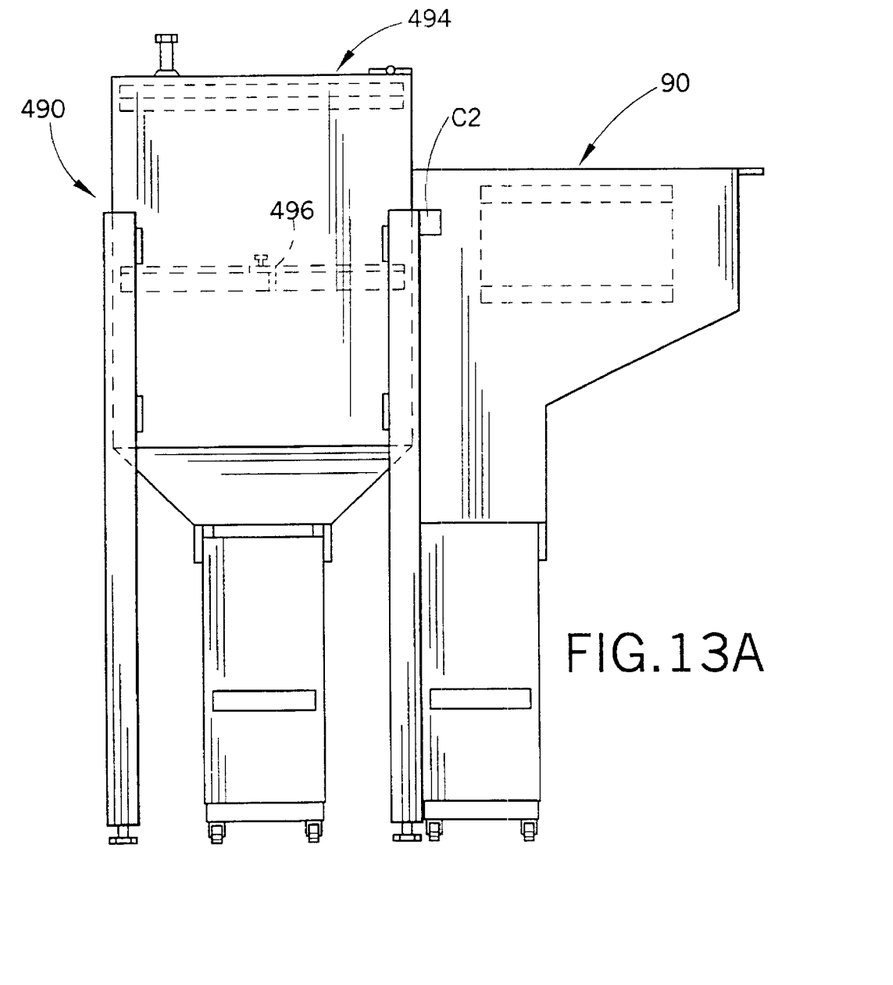
FIG. 13A illustrates a three-dimensional specimen target chamber as it is releasably connected to a two-dimensional specimen modular target chamber for purposes of testing three-dimensional specimens.
Figure 13B:
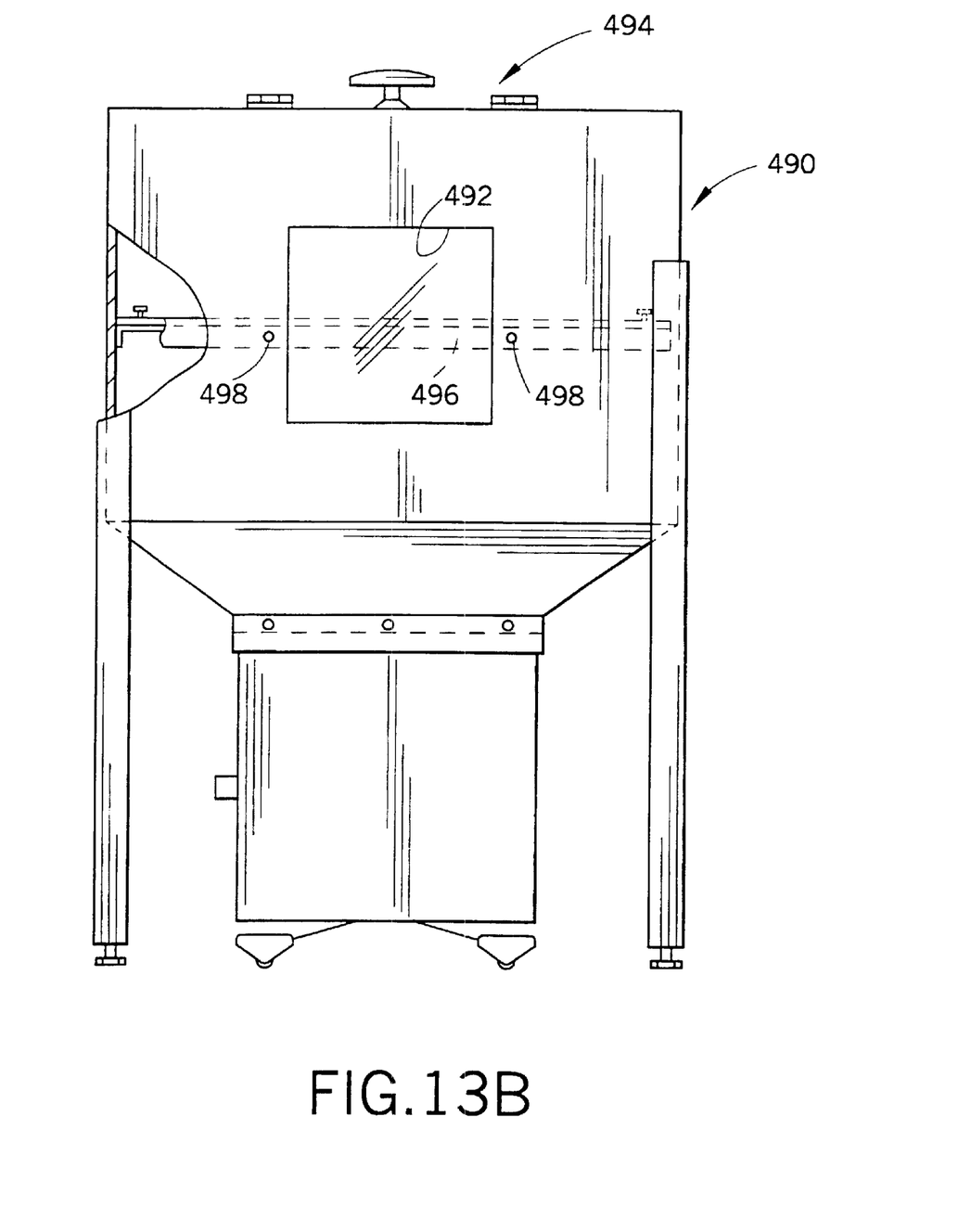
FIG. 13B is a left side elevational view of the three-dimensional specimen target chamber shown in FIG. 13A; and, FIG. 13C is a top plan view of the three-dimensional specimen target chamber releasably connected to a two-dimensional specimen target chamber.
Figure 13C:
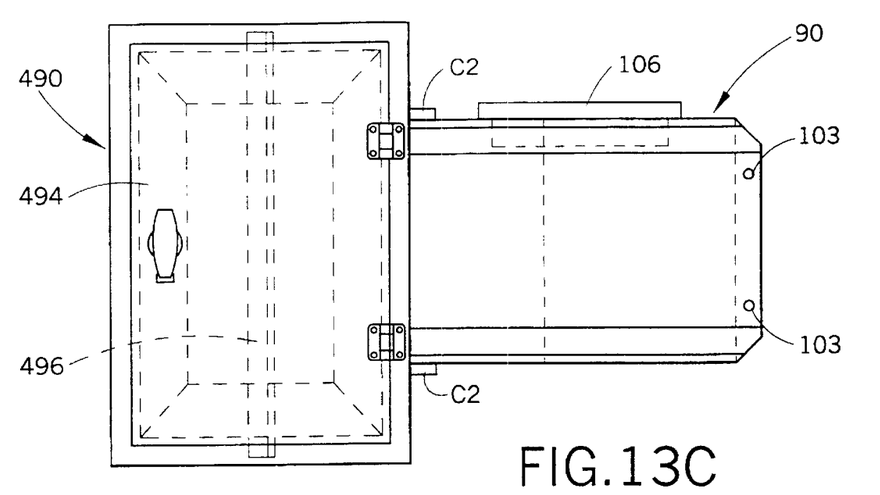

FIGS. 13A–13C depict a modular three-dimensional specimen target chamber 490 in accordance with the present invention. The three-dimensional specimen target chamber 490 is selectively and releasably clamped or otherwise fastened to one of the modular 90° target chambers 90,190 and includes a media inlet 492 which communicates with the target chamber specimen window 96,196. Rather than securing a two-dimensional panel or other specimen in the window 96,196, the window is left open and a three-dimensional specimen, such as a spring, wheel cover, or the like, is positioned in the three-dimensional specimen target chamber 490. The specimen is placed in the chamber 490 through a hinged access door 494. The chamber 490 preferably also includes an adjustable clamping bar 496 movable toward and away from the window 492 or other like means for fixedly securing a specimen is a desired location in line with the window 492. The media propelled by a gun 54,54' passes through the chamber 90,190 and into the three-dimensional target chamber to impinge on the three-dimensional specimen housed therein. The modular three-dimensional specimen chamber 490 is selectively and releasably connected to one of the 90° two-dimensional specimen chambers 90,190 using manually operable retainers such as clips C2 that selectively engage studs 498, or through use of interlocking parts of the chambers 90,490, bolts, pins, clamps, or any other suitable connectors.

The invention has been described with reference to preferred embodiments. Obviously, modifications and alterations will occur to to hers upon a reading and understanding of the preceding specification. It is intended that the invention be construed as including all such modifications and alterations insofar as they fall within the scope of the appended claims and equivalents thereof.

Having thus described the preferred embodiments, the invention is claimed to be:

1. A multi-test gravelometer for performing coating testing operations in accordance with at least two different standards as desired by a user, said gravelometer comprising:

first and second media guns constructed according to respective first and second different testing standards;

a frame including a mount for individually releasably receiving and retaining said first and second media guns in an operative position wherein a media inlet of said releasably retained gun is positioned to receive testing media and a media outlet of said releasably retained gun is positioned to project testing media toward a testing target on a target path;

a compressed air supply adapted for communication with an air inlet of said releasably retained gun;

at least two different target chambers for supporting a test specimen in a required orientation for impingement by media traveling on said target path, said at least two different target chambers respectively constructed according to at least two different testing standards including said first and second testing standards, said at least two different target chambers adapted for being individually releasably and operatively connected to said frame to receive media traveling on said target path.

2. The multi-test gravelometer as set forth in claim 1 further comprising:

a media supply system connected to said frame, said media supply system including a media hopper for containing a supply of testing media and a media feeder for communicating testing media from the hopper to the medial inlet of the associated media gun secured to said frame.

3. The multi-test gravelometer as set forth in claim 2 wherein said media feeder comprises a vibratory feeder.

4. The multi-test gravelometer as set forth in claim 1 further comprising:

at least one clamp connected to said frame and adapted for selectively engaging a radially enlarged flange portion of said associated media gun, said at least one clamp, when closed, fixedly securing said flange in abutment with said frame.

5. The multi-test gravelometer as set forth in claim 1 further comprising:

a plurality of locator pins extending from said frame for engagement with mating apertures of each of said at least two target chambers; and, a plurality of retaining clips for selectively and releasably interconnecting each of said at least two target chambers to said frame.

6. The multi-test gravelometer as set forth in claim 1, wherein said at least two target chambers comprise:

a two-dimensional specimen target chamber selectively, operatively, and releasably secured to said frame; and, a three-dimensional specimen target chamber selectively, operatively, and releasably connected to said two-dimensional specimen target chamber, said three-dimensional specimen chamber adapted to receive and support a three-dimensional target specimen for impingement by media traveling on said target path.

7. A multi-test gravelometer for performing coating testing operations in accordance with at least two different standards as desired by a user, said gravelometer comprising:

a frame adapted to receive and selectively releasably retain, individually, both an SAE compliant media gun and a VDA compliant media gun in an operative position wherein a media inlet of said selectively received and retained gun is positioned to receive testing media and a media outlet of said associated gun is positioned to project testing media toward a testing target;

a compressed air supply adapted for communication with an air inlet of said associated gun; and, means for releasably securing any one of a plurality of different two-dimensional specimen target chambers to said frame in an operative position so that the media outlet of an associated gun is directed into and enclosed by an interior portion of an operatively secured target chamber in line with a target specimen support region thereof.

8. A method of constructing a gravelometer apparatus to perform testing in accordance with either of at least two different testing standards, as desired, said method comprising:

selecting a first media projecting gun to perform testing in accordance with a first testing standard;

selecting a second media gun to perform testing in accordance with a second testing standard, said first and second guns conformed differently in accordance with said first and second testing standards;

operatively and releasably securing said first media gun to a frame member and to a source of compressed air to perform testing in accordance with said first testing standard or operatively and releasably securing said second media gun to said frame member and to said source of compressed air to perform testing in accordance with said second testing standard;

selecting one of a plurality of different target chambers based upon which of said first and second media guns is operatively and releasably secured to said frame member; and, operatively and releasably securing said selected one of said target chambers to said frame member.

9. A method of testing a coating on a target specimen according to at least two different standards, said method comprising:

(a) selecting one of a plurality of testing standards for testing coating properties;

(b) selecting testing media in accordance with said selected testing standard;

(c) selecting one of a plurality of different media projecting guns so that said selected gun complies with said selected testing standard;

(d) operatively and releasably securing said selected media gun to a frame member;

(e) selecting one of a plurality of different target chambers which corresponds to said selected media gun and said selected testing standard;

(f) operatively and releasably securing said selected target chamber to said frame member so that a testing media outlet of said operatively secured media gun is directed into an interior portion thereof along a target path;

(g) connecting a fluid inlet of said operatively secured media gun to a supply of compressed fluid;

(h) selecting a target specimen and operatively securing said target specimen to said selected target chamber in line with said target path;

(i) selectively feeding said selected testing media to a media inlet of said operatively secured media gun and selectively communicating compressed fluid from said supply to said fluid inlet of said operatively secured media gun so that said operatively secured media gun projects said selected testing media outwardly from its outlet along said target path for impingement on said operatively secured target specimen; and, (j) repeating steps (b)–(i) for at least two different testing standards selected from said plurality of testing standards in step (a).

10. A multi-test gravelometer apparatus comprising:

a frame comprising a mount;

first and second different media guns for propelling test media under force of compressed air on a target path, said first and second media guns constructed according to first-and second different testing standards, respectively, said first and second different media guns selectively individually operatively connected to said frame by said mount and each comprising; (i) a media inlet; (ii) a media outlet; and, (iii) a compressed air inlet; and, first and second different specimen target chambers constructed according to said first and second different standards, respectively, said first and second target chambers selectively individually and operably connected to said frame in an operative position, each of said first and second target chambers including a specimen support in line with said target path, said specimen support adapted to support a target specimen for impingement by media traveling on said target path.

* * * * *